US008857212B2

(12) United States Patent
Van Sint Annaland et al.

(10) Patent No.: US 8,857,212 B2
(45) Date of Patent: Oct. 14, 2014

(54) PROCESS FOR THE SEPARATION OF CONTAMINANT OR MIXTURE OF CONTAMINANTS FROM A CH4-COMPRISING GASEOUS FEED STREAM (75) Inventors: Martin Van Sint Annaland, Eindhoven (NL); Martin Jan Tuinier, Eindhoven (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/881,228

(22) PCT Filed: Oct. 10, 2011

(86) PCT No.: PCT/EP2011/067651
§ 371 (c)(1),
(2), (4) Date: Jul. 8, 2013

(87) PCT Pub. No.: WO2012/055695
PCT Pub. Date: May 3, 2012

(65) Prior Publication Data
US 2013/0296627 A1    Nov. 7, 2013

(30) Foreign Application Priority Data
Oct. 26, 2010 (EP) .................................... 10188933

(51) Int. Cl.
*B01D 53/00* (2006.01)
*C07C 7/14* (2006.01)

(52) U.S. Cl.
CPC ................. *C07C 7/14* (2013.01); *Y02E 50/346* (2013.01); *B01D 2257/504* (2013.01); *B01D 53/002* (2013.01); *B01D 2256/24* (2013.01); *Y10S 62/928* (2013.01)
USPC ................... 62/602; 62/601; 62/928; 62/532; 585/812

(58) Field of Classification Search
None
See application file for complete search history.

(56) References Cited

U.S. PATENT DOCUMENTS
4,265,088 A    5/1981   Funk
6,082,133 A    7/2000   Barclay et al.
(Continued)

FOREIGN PATENT DOCUMENTS
WO    2009047341    4/2009

OTHER PUBLICATIONS

Grande, C.A. et al.; "Biogas to Fuel by Vacuum Pressure Wing Adsorption I. Behavior of Equilibrium and Kinetic-Based Adsorbents"; Ind. Eng. Chem; Res. 46; pp. 4595-4605; 2007.
Tuinier, M.J. et al., "Crogenic CO2 Capture Using Dynamically Operated Packed Beds", Chemical Engineering Science, vol. 65, 2020, pp. 114-119.

*Primary Examiner* — Tam M Nguyen (57) ABSTRACT

The invention provides a process for the separation of a contaminant or mixture of contaminants from a $CH_4$-comprising gaseous feed stream, comprising the subsequent steps of: a) passing a $CH_4$-comprising gaseous feed stream comprising the contaminant or the mixture of contaminants into and through a cold porous body having a temperature below the sublimation temperature of the contaminant or the mixture of contaminants and contacting the $CH_4$-comprising gaseous feed stream at elevated pressure with the surface of the cold porous body to obtain a porous body comprising solid contaminant or mixture of contaminants and a contaminant-depleted product gas; and b) reducing the pressure to obtain fluid contaminant or mixture of contaminants and a cold porous body. c) removing the fluid contaminant or mixture of contaminants, wherein the contaminant is selected from $CO_2$, hydrogen sulphide, mercaptans, siloxanes and carbonyl sulphide, or a mixture thereof.

13 Claims, 6 Drawing Sheets

(56) References Cited

U.S. PATENT DOCUMENTS

| | | | |
|---|---|---|---|
| 6,962,629 B2 * | 11/2005 | Johnson et al. | 134/13 |
| 7,073,348 B2 | 7/2006 | Clodic et al. | |
| 7,402,198 B2 * | 7/2008 | Mori et al. | 96/108 |
| 8,138,381 B2 * | 3/2012 | Joshi et al. | 568/910 |
| 2009/0200211 A1 * | 8/2009 | Taylor | 208/409 |
| 2009/0286890 A1 * | 11/2009 | Joshi et al. | 518/701 |
| 2010/0024471 A1 | 2/2010 | Hees et al. | |
| 2011/0023537 A1 * | 2/2011 | Assink et al. | 62/617 |

* cited by examiner

PROCESS FOR THE SEPARATION OF CONTAMINANT OR MIXTURE OF CONTAMINANTS FROM A CH4-COMPRISING GASEOUS FEED STREAM

PRIORITY CLAIM

The present application claims priority from PCT/EP2011/067651, filed 10 October, which claims priority from European application 10188933.5, filed 26 Oct. 2010, which is incorporated herein by reference.

FIELD OF THE INVENTION

The present invention provides a process for the separation of contaminants or a mixture of contaminants from a $CH_4$-comprising gaseous feed stream.

BACKGROUND OF THE INVENTION

Landfill gas (LFG) is formed due to anaerobic decomposition of organic waste material at landfill sites. LFG mainly consists of $CH_4$ and $CO_2$, both known as greenhouse gases. Cheapest option to avoid emissions is to collect LFG and send it to a flare. However LFG has the potential to serve as a renewable energy resource, as $CH_4$ is a valuable component. To convert LFG to commercial grade $CH_4$, several separation and purification steps are required, e.g. removing the contaminants $CO_2$, $H_2O$, and sometimes $H_2S$.

Several separation technologies are being applied or researched in the field of biogas treatment, such as adsorption, membranes and cryogenics. Every technology has its advantages and drawbacks.

One particular widely applied separation technology is adsorption. Separation of for instance $CO_2$ from gas mixtures by adsorption is based on differences in equilibrium capacities at the adsorbent surface (e.g. zeolite 13X) or on differences in uptake rates (e.g. carbon molecular sieve 3K). An adsorption process normally consists of three packed beds, which are operated in different cycles, e.g. adsorption, evacuation, repressurization and product rinse steps. In Grande and Rodrigues, (Grande C. A., Rodrigues A. E., (2007), Biogas to Fuel by Vacuum Pressure Swing Adsorption I. Behavior of Equilibrium and Kinetic-Based Adsorbents. Ind. Eng. Chem. Res., 46, 4595-4605), a Vacuum Pressure Swing Adsorption process is described with two different adsorbents, i.e. carbon molecular sieve 3K and zeolite 13X to separate $CO_2$ from $CH_4$. A disadvantage of this process is the relatively low purity of the obtained $CH_4$ and the high energy consumption. In addition, in the process of Grande and Rodrigues it is assumed that water and other contaminants have been previously removed, as these compounds may interfere with the sorption of the $CO_2$.

Other processes make use of the triple point of $CO_2$, which is approximately 5.2 bara and $-56.7°$ C., and the fact that liquid $CO_2$ can only exist at certain temperatures and pressures above the $CO_2$ triple point.

In U.S. Pat. No. 7,073,348 is disclosed a process for the capture of $CO_2$ from flue gas at atmospheric pressure by contacting the flue gas with the external surface of a heat exchanger, while evaporating a refrigerant fluid on the inside. Solid $CO_2$ is deposited on the external walls of the heat exchanger. After a certain operating time, the flow of flue gas on the external part of the exchanger and refrigerant fluid on the inside of the exchanger are respectively switched over to a second parallel heat exchanger. The solid $CO_2$ deposited on the externals surface of the first heat exchanger is reheated from $-78.5°$ C. to $-56.5°$ C. at a pressure of 5.2 bar and the $CO_2$ is retrieved as a liquid phase.

Heat exchangers are expensive and have limited area available for heat exchange and deposition of the solid $CO_2$. As the refrigerant continuously provides cold to the evaporator surface, most of the $CO_2$ will deposit on the upstream side of the evaporator, resulting in an inhomogeneous distribution of the solid $CO_2$. Also, due to the build up of the solid $CO_2$ layer the pressure drop over the evaporator is increased significantly during operation. Furthermore, the resistance to heat transfer is increased with the increasing thickness of the deposited solid $CO_2$ layer, resulting in an inefficient use of the refrigerant. Consequently, it is necessary to operate the expensive and relatively sensitive evaporator apparatus at short deposit/removal cycles thereby exposing the evaporator apparatus to rapid changes in temperature, which is disadvantageous from a mechanical point of view.

U.S. Pat. No. 4,265,088 discloses a process for treating hot exhaust gas using two or more packed towers. In the process of U.S. Pat. No. 4,265,088, the hot exhaust gas is introduced in a packed tower, which was cooled to a temperature below the sublimation temperature of $CO_2$. The $CO_2$ is sublimated and thereby captured from the exhaust gas. The sublimated solid $CO_2$ is subsequently removed from the packed tower by applying a vacuum to the packed tower to induce evaporation of the solid $CO_2$. However, such a process can only be used for treating exhaust gases containing low concentrations of $CO_2$. When the exhaust gas contains high concentrations of $CO_2$ the use of a vacuum becomes impractical. Alternatively, U.S. Pat. No. 4,265,088 discloses the use of treated exhaust gas to remove the solid $CO_2$ from the packed tower. However, this has the disadvantage that $CO_2$ is reintroduced in at least part of the treated exhaust gas.

In WO2009047341, a process for separating $CO_2$ from a flue gas is described, which is based on dynamic operation of three parallel packed beds, which are operated in cooling, capture and recovery cycles. In the process of WO2009047341, the flue gas is contacted with a fixed bed of cold particles on which the $CO_2$ sublimates as a solid. Subsequently, the particles with solid $CO_2$ thereon are contacted with a warm gas to heat the particles and evaporate the carbon dioxide. Finally, the heated particles are cooled again.

The process of WO2009047341 is focused on retrieving pure $CO_2$ and therefore the warm gas applied to heat the particles with solid $CO_2$ thereon is itself essentially pure $CO_2$. This results in the need to operate the process in three separate cyclic steps each performed in a separate fixed bed, wherein in the middle step the packed bed $CO_2$ is removed exposing the solid $CO_2$ to temperatures above the sublimation temperature, thereby increasing the temperature of the packed bed, while in the latter step it is required to cool the heated fixed bed back to a temperature below the sublimation temperature of $CO_2$.

There is a need in the art for a process to purify $CH_4$-comprising gases such as landfill gas, which is simpler, less energy intensive and allows for the production of high purity $CH_4$.

SUMMARY OF THE INVENTION

It has new been found that it is possible to purify $CH_4$-comprising gases such as landfill gas, by removing at least $CO_2$, without the disadvantages mentioned herein above. Similarly, $CH_4$-comprising gases may be purified from contaminants such as hydrogen sulphide ($H_2S$), mercaptans (or thiols, RSH), siloxanes and carbonyl sulphide (COS).

Accordingly, the present invention provides a process for the separation of a contaminant or mixture of contaminants from a $CH_4$-comprising gaseous feed stream, comprising the subsequent steps of:

a) passing a $CH_4$-comprising gaseous feed stream comprising the contaminant or the mixture of contaminants into and through a cold porous body having a temperature below the sublimation temperature of the contaminant or the mixture of contaminants and contacting the $CH_4$-comprising gaseous feed stream at elevated pressure with the surface of the cold porous body to obtain a porous body comprising solid contaminant or mixture of contaminants and a contaminant-depleted product gas; and b) reducing the pressure to obtain fluid contaminant or mixture of contaminants and a cold porous body.

c) removing the fluid contaminant or mixture of contaminants, wherein the contaminant is selected from $CO_2$, hydrogen sulphide, mercaptans, siloxanes and carbonyl sulphide, or a mixture thereof. In particular, the present invention provides a process for the separation of $CO_2$ from a $CH_4$-comprising gaseous feed stream, comprising the subsequent steps of:

a) passing a $CH_4$-comprising gaseous feed stream comprising $CO_2$ into and through a cold porous body having a temperature below the sublimation temperature of $CO_2$ and contacting the $CH_4$-comprising gaseous feed stream at a pressure of at least 4 bar absolute with the surface of the cold porous body to obtain a porous body comprising solid $CO_2$ and a $CO_2$-depleted product gas; and b) reducing the pressure by at least 2 bar to obtain fluid $CO_2$ and a cold porous body.

c) removing the fluid $CO_2$. The process according to the present invention makes use of a previously cooled porous body having surface to deposit $CO_2$. Such a porous body can only store a limited amount of cold and therefore the amount of $CO_2$ that can be deposited is also limited. As a consequence, no large build-up of $CO_2$ deposits can occur and the creation of a pressure drop over the separator is to a large extent prevented.

By using a porous body, a large specific surface area per unit volume may be available for heat exchange and $CO_2$ deposition. This may result in an improved efficiency of the process.

By allowing the pressure to drop by at least 2 bar in step (b) the solid $CO_2$ evaporates, while at the same time the porous body is cooled. This significantly reduces the amount of energy required to cool the porous body back to a temperature below the sublimation temperature of $CO_2$ so that the porous body may be reused in step (a).

The process can be operated, using relatively simple process apparatus limiting the capital cost compared to the expensive evaporators used in the prior art process. In addition the process can be operated using only two separate parallel fixed beds.

DETAILED DESCRIPTION OF THE INVENTION

The present invention relates to the use of a cold porous body for example to separate $CO_2$ from a $CH_4$-comprising gaseous feed streams comprising $CO_2$. The cold porous body is contacted with the $CH_4$-comprising gaseous feed streams, whereby the cold porous body is used as an intermediate energy repository, i.e. it stores a finite amount of energy, which is used to sublimate $CO_2$. In contrast, known heat exchangers transfer heat substantially instantaneously, i.e. no intermediate storage of energy takes place. Similarly, contaminants such as hydrogen sulphide ($H_2S$), mercaptans (or thiols, RSH), siloxanes and carbonyl sulphide (COS) may be separated from $CH_4$-comprising gaseous feed streams.

It will be appreciated that heat transfer is, at least in part, dependent on the available surface area for heat transfer. Typically, a plate heat exchanger has a specific surface area of approximately 500 $m^2/m^3$. Monolithic packings can have much higher specific surface areas, which can be as high as 3500 $m^2/m^3$ or even higher.

In step (a) of the process according to the invention, also referred to as the capture cycle, the $CH_4$-comprising gaseous feed stream is contacted with the cold body at a pressure of 4 bar absolute or higher of $CO_2$, preferably at a pressure in the range of from 4 to 50 bar absolute, more preferably 5 to 40 bar absolute, even more preferably 5 to 15 bar absolute. The temperature of the cold body is below the triple point temperature. The $CO_2$ in the $CH_4$-comprising gaseous feed stream is sublimated and deposited on the surface of the cold body as solid $CO_2$, thereby obtaining a porous body comprising solid $CO_2$. As $CO_2$ is deposited on the cold porous body, the temperature of the cold porous body increases. Reference herein to sublimation is to the phase transition of a gas to a solid or of a solid to a gas, without the existence of a liquid phase. It should be noted that pure $CO_2$ has a sublimation temperature of approximately $-78°$ C. at atmospheric pressure, when diluted the sublimation temperature decreases. Typically, a flue gas containing 20 vol % $CO_2$ will have a sublimation temperature of approximately $-93°$ C. at atmospheric pressure. Reference in herein to the sublimation temperature of $CO_2$, therefore, will always be to the sublimation temperature of $CO_2$ under the existing process conditions.

The $CH_4$-comprising gaseous feed stream is contacted with the cold porous body by passing it into and through the porous body. A $CO_2$-depleted product gas is obtained exiting the porous body.

When sufficient $CO_2$ has been deposited in the cold porous body, the capture cycle is ended and the supply of $CH_4$-comprising gaseous feed is halted. In step (b) of the process according to the invention the solid $CO_2$ is subsequently removed from the surface of the porous body comprising solid $CO_2$ by reducing the pressure to which the porous body is exposed to in step (a) by at least 2 bar. By reducing the pressure, the solid $CO_2$ evaporates to give fluid $CO_2$, preferably gaseous $CO_2$. In addition, the porous body from which the solid $CO_2$ is evaporated cools, as the heat for evaporation is withdrawn from the porous body. As a result the temperature of the porous body after evaporation is lowered compared to the temperature of the porous body comprising solid $CO_2$ obtained from step (a). Preferably, the cold porous body obtained in step (b) has a temperature below the sublimation temperature of $CO_2$, i.e. the sublimation temperature of $CO_2$ corresponding to the process conditions of step (a). This provides a significant advantage over the prior art cryogenic processes, such as for example described in WO2009047341, where the solid $CO_2$ is evaporated by heating the porous body comprising solid $CO_2$. In case the porous body comprising solid $CO_2$ is heated to evaporate the $CO_2$, the obtained porous body after evaporation has a temperature above the temperature of the porous body comprising solid $CO_2$ obtained from step (a). As a result, the prior art cryogenic process requires significantly more energy to re-cool the porous medium if the porous medium is to be recycled to step (a).

Preferably, the pressure is reduced in step (b) by in the range of from 2 to 49 bar, more preferably 4 to 39 bar depending on the pressure at which the cold porous medium was contacted with the $CH_4$-comprising gaseous feed stream in step (a). Even more preferably, the pressure is reduced to atmospheric pressure. This will in all cases be the largest pressure difference, which can be achieved without the requirement to provide for additional means such as a vacuum pump. By allowing the maximum pressure reduction to occur, the combined effect of evaporation and simultaneous cooling is optimised.

Preferably, the pressure reduction is effectuated in a short period, preferably in a time period of at most 30 seconds, more preferably at most 10 seconds, still more preferably at most 1 second, whereby the lower time limit is the minimum time required to effectuate the desired pressure reduction and is set by the design of the porous body and constrains of any apparatus holding the porous body. The pressure may be reduced by flashing the cold porous body comprising solid $CO_2$ to the desired pressure, preferably atmospheric pressure. By flashing the cold porous body comprising solid $CO_2$ a fast reduction of the pressure is achieved.

The fluid $CO_2$ obtained in step (b) is removed in step (c) of the invention. Preferably, the fluid $CO_2$ is removed by flushing the cold porous body with a fluid stream, preferably a gaseous stream. Preferably, the fluid stream used to flush the cold porous body does not comprise a significant concentration of fluids or gases having a sublimation temperature equal to or higher than the sublimation temperature of $CO_2$ under the conditions at which it is contacted with the cold porous body obtained in step (b). Reference herein to a significant concentration is to a concentration of more than 5 vol %, preferably more than 1 vol %, more preferably more than 0.5 vol % based on the volume of the fluid stream used to flush the cold porous body. Such gases may form solid deposits on the cold porous body obtained in step (b). Preferred gaseous components of the gas stream used to flush the cold porous body include but are not limited to $N_2$, $H_2$, He, Ne, Ar, Kr, $CH_4$ or a mixture comprising one or more thereof. A preferred fluid stream comprises dry air. Although, air does comprise some $CO_2$, its concentration is not significant for the process according to the invention. Dry air is preferred over air that is not dry, due to the fact that any $H_2O$ in the air may be undesirably deposited on the cold porous body obtained in step (b). Reference herein to dry air is to air comprising less than 1 vol %, more preferably 0.5 vol %, and even more preferably less than 0.05 vol % of $H_2O$, based on the volume of the dry air. Typically the vapor pressure of $H_2O$ at for instance $-110°$ C. is $3.6 \cdot 10^{-9}$ bar, therefore air of $-110°$ C. at atmospheric pressure can almost not contain any water (ppb level). So when air is cooled down to form the cold liquid most or almost all of the $H_2O$ will be condensed or freezed-out in the air cooler. Optionally, the air is first dried prior to being cooled to prevent accumulation of ice in the cooling device used to cool the air.

Preferably, the cold porous body is flushed by passing the fluid stream used to flush the cold porous body into and through the cold porous body.

As mentioned herein above, during the pressure release of step (b), the porous body is cooled as it provides the heat of evaporation for the $CO_2$. Although the temperature of the porous body may be lowered to a temperature below the sublimation temperature of $CO_2$, i.e. the sublimation temperature of $CO_2$ corresponding to the process conditions of step (a), and could therefore be directly used in a subsequent step (a) of the process, it may be preferably to, in a further step (d) of the process, further cool the porous body, more preferably to cool the porous body to a temperature close to or even essentially equal the original temperature of the cold porous body having a temperature below the sublimation temperature at the beginning of step (a). This may be done by passing a cold fluid stream, preferably a cold gaseous stream, having a temperature below the sublimation temperature of $CO_2$, into and through the cold porous body to further cool the cold porous body.

The cold fluid stream may be any suitable cold fluid, preferably a cold gas. More preferably the cold fluid is the fluid stream used to flush the cold porous body in step (c). In that case step (c) and (d) may combined to simultaneously remove the fluid carbon dioxide and further cool the cold porous body by providing a fluid stream having a temperature below the sublimation temperature of $CO_2$ into and through the cold porous body. It will be appreciated that the cold fluid must be provided in sufficient quantities to be able to cool the porous body. Furthermore, the temperature of the cold fluid must be below the sublimation temperature of $CO_2$. In order to sufficiently cool the porous body, the cold fluid may preferably have a temperature in the range of from $-200$ to $-90°$ C., more preferably of from $-175$ to $-100°$ C. If simultaneous deep hydrogen sulphide removal is considered, initial temperatures of the porous body may be required as low as $-150°$ C.

The cold fluid may be passed into and through porous body in any direction. As the cold fluid passes through the porous body it will heat. However, the fluid stream exiting the porous body will still be relatively cold, i.e. colder than ambient air, optionally still cooler than the desired temperature of the porous body, i.e. a temperature suitable to be used in step (a). Therefore, it is preferred to recycle the cold fluid exiting the porous body in step (d) back to the porous body. Preferably, the cold fluid exiting the porous body in step (d) is cooled prior to being recycled to the porous body. In case step (c) and (d) are combined, the initial cold fluid exiting the porous body in step (d) will comprise the fluid $CO_2$ removed from the porous body. This $CO_2$-comprising cold fluid is not recycled, but otherwise disposed of. After the $CO_2$ content of the cold fluid exiting the porous body is sufficiently low, the recycle of cold fluid exiting the porous body in step (d) may be initiated.

Preferably, where the $CH_4$-comprising gaseous feed stream comprising $CO_2$ is passed into and through the cold porous body in step (a) in a first flow direction, cold fluid stream is passed into and through the cold porous body in step (c) and/or (d) in a flow direction which is the same (also referred to a co-current mode) or opposite (also referred to a counter-current mode) to the flow direction of the $CH_4$-comprising gaseous feed stream. As the $CH_4$-comprising gaseous feed stream is passed into and through the cold porous body, a temperature profile is formed in the cold porous body from a cold zone to a hot zone in a direction opposite to the flow direction of the $CH_4$-comprising gaseous feed stream. This temperature profile is created due to the fact that the $CH_4$-comprising gaseous feed stream is warm compared to the cold porous medium and will heat the cold porous medium, forming a hot zone at the entrance of the porous body. When the cold fluid provided in step (c) and/or (d) is passed into and through the porous medium in the same direction as the $CH_4$-comprising gaseous feed stream the hot zone will pass through the entire length of the porous medium. Therefore, preferably, the cold fluid stream is passed into and through the cold porous body in step (c) and/or (d) in a flow direction which is the opposite to the flow direction of the $CH_4$-comprising gaseous feed stream. As a result, there is no need for the hot zone to pass through the entire length of the porous medium, but rather exit the porous medium at a hot side of the porous medium.

In the process according to the invention, step (a) wherein $CO_2$ is deposited on the cold porous body, is also referred to as the capture cycle or $CO_2$ capture cycle, while steps (b), (c) and optionally (d) are referred to as the $CO_2$ removal and cooling cycle or $CO_2$ recovery and cooling cycle.

During step (a) of the process, the $CH_4$-comprising gaseous feed stream is passed into and through the cold porous body by providing a flow of $CH_4$-comprising gaseous feed stream to the cold porous body. Prior reducing the pressure in step (b), the flow of the $CH_4$-comprising gaseous feed stream to the porous body, i.e. in step (b) the porous body comprising solid $CO_2$, is halted. The remaining $CH_4$-comprising gaseous feed in the porous body at the time the pressure is released may be removed from porous body together with the fluid $CO_2$ in a subsequent step (c). Alternatively, the remaining $CH_4$-comprising gaseous feed in the porous body at the time the flow of $CH_4$-comprising gaseous feed to the porous body is halted is flushed from the porous body while the body is still at pressure. Only after the remaining $CH_4$-comprising gaseous feed has been removed, is the pressure reduced according to step (b) of the process. Preferably, the remaining $CH_4$-comprising gaseous feed in the porous body is flushed by passing the cold fluid stream into and through the porous medium comprising solid $CO_2$ at a pressure equal to the $CH_4$-comprising gaseous feed stream until at least part of the remaining $CH_4$-comprising gaseous feed in the porous body has been flushed. Subsequently, the pressure is reduced according to step (b) of the invention. This has the advantage that less $CH_4$ is lost with the fluid $CO_2$ in step (c).

Preferably, steps (b), (c) and preferably also step (d) are combined by reducing the pressure to which the porous body comprising solid $CO_2$ was exposed in step (a) by providing a cold fluid having a pressure which is at least 2 bar lower and than the pressure to which the porous body comprising solid $CO_2$ was exposed in step (a).

Preferably, the porous body is in the form of a fixed bed. Preferably, the porous body is a monolith, for example a ceramic foam. In an equally preferred embodiment, the porous body is comprised of particles, preferably monolithic particles. Optionally, the particles are sintered to each other. Such porous bodies may provide the high specific surface areas, which are beneficial for the heat exchange and the available area for $CO_2$ deposition. Advantages of using monoliths include a lower pressure drop and less axial dispersion of the mass front and in particular the heat front through the porous body.

The process allows for the continuous separation of $CO_2$ from the $CH_4$-comprising gaseous feed stream. Using the cold body in the form of dynamically operated fixed beds, the porous body is used as an intermediate energy repository. Accordingly, the process may be operated in a continuous way by providing at least two porous bodies in the form of two fixed beds, more than two is allowed, but not necessary. The beds are passed/through a cycle of:
i) steps (a); and
ii) (b), (c) and optionally (d),
simultaneously.

The fixed beds are operated out of phase, i.e. at any one time one bed is operating step a) ($CO_2$ capture cycle), and one bed is operating a sequence of steps (b), (c) and optionally (d) ($CO_2$ removal and cooling cycle). When the bed that is operating step (a) is full, it is switched to the sequence of steps (b), (c) and optionally (d) and the other bed is switched accordingly.

The fixed bed may be any type of fixed bed. The fixed bed may be in the form of a separate entity; a plurality of fixed beds operated in series or parallel, or may be formed by a part, zone or section of a larger fixed bed arrangement.

When a fixed bed is used, solid $CO_2$ is deposited in the fixed bed during step (a) of the process according to the invention. It should however be noted that this does not lead to a significantly increased pressure drop or even clogging of the fixed bed. This is due to the limited amount of energy, also referred to as cold duty, that is stored at any location throughout the fixed bed. For $CO_2$ sublimation with an initial temperature of $-110°$ C., the maximum $CO_2$ mass deposition is below 50 kg per cubic meter of porous body, depending on the volumetric heat capacity of the solid material. Assuming that the porous body comprising solid $CO_2$ has a density of about 1000-1500 $kg/m^3$, depending on the porosity of the deposited $CO_2$ layer, this corresponds to 3-5 vol %. Such volume can easily be stored in a structured or unstructured packing, which can easily have porosities exceeding 20 vol % or more than 30 vol %. Thus, problems with plugging or unacceptable pressure drop increase during the capture cycle can be intrinsically circumvented. This is one of the major advantages of the process according to the invention.

The process according to the present invention can be used to remove $CO_2$ from any $CH_4$-comprising gaseous feed stream comprising $CO_2$, such as landfill gas or natural gas. Preferably, the gaseous feed stream comprises at least 3 vol % $CO_2$, preferably in the range of from 5 to 75 vol % of $CO_2$, more preferably 10 to 35 vol % of $CO_2$. In order to maximise the effectiveness of the $CO_2$ separation by sublimation, it is preferred that other gaseous compounds in the $CH_4$-comprising gaseous feed stream have a condensation or sublimation temperature below the temperature of the cold porous body. Suitable examples of other gaseous compounds include $N_2$, $O_2$, $H_2$, $CH_4$. Notwithstanding the above, the $CH_4$-comprising gaseous feed may also contain $H_2S$. The conditions under which the $CO_2$ sublimates are also suitable to capture $H_2S$, of which the condensation temperature is approximately $-60°$ C. and the solidification temperature is approximately $-82°$ C. at 1 bar. Therefore the process according to the invention can also be used to remove $H_2S$ from the $CH_4$-comprising gaseous feed. Preferably, the $CH_4$-comprising gaseous feed comprises in the range of from 0 to 40 vol % of $H_2S$, more preferably 0 to 20 vol % of $H_2S$ and even more preferred 0 to 5 vol % of $H_2S$. It is noted herein that the process according to the present invention can also be used to remove $H_2S$ from a gas stream, which does not comprise carbon dioxide.

Notwithstanding the above, the $CH_4$-comprising gaseous feed may also contain a variety of contaminants and trace compounds, in particular mercaptans, carbonyl sulphide and components such as halides and silicon containing compounds (e.g. siloxanes), which also may be removed from the gaseous feed using the method according to the invention. The initial temperature of the porous body should be selected such that it is below the condensation temperature of the compound which is to be removed.

If the $CH_4$-comprising gaseous feed stream comprises $H_2O$, it may be beneficial to first dehydrate the gaseous feed stream, preferably such that in the range of from 80 wt % to 100 wt % or substantially 100 wt %, based on the total $H_2O$ present, is removed. More preferably 90 to 99.9 wt %, even more preferably 95 to 99.5 wt % of the $H_2O$ is removed. However, it is not necessary to pre-treat the gaseous feed to remove $H_2O$. In case $H_2O$ is present in the gaseous feed stream to the process according to the invention it is possible to remove, i.e. separate from the gaseous feed stream, the $H_2O$, together with the $CO_2$. The conditions under which the $CO_2$ sublimates are also suitable to capture $H_2O$, which condensates and solidifies at temperatures well above the sublimation temperature of $CO_2$. Therefore the process according to the invention can also be used to remove $H_2O$ from the $CH_4$-comprising gaseous feed. In order to achieve an efficient removal of $H_2O$ from the porous body it is preferred that the pressure is reduced by at least 10 bar in step (b). Due to the very low vapour pressure of water at low temperatures, it may not be possible to remove all the water by a pressure reduction. Therefore, preferably, the porous body is periodically subjected to a separate heat treatment to remove any water that was deposited during the normal operation of the process according to the invention. The process according to the present invention therefore provides the advantage that less $H_2O$, or even no $H_2O$, needs to be removed from the gaseous feed stream prior to being processed in the process according to the invention. A subsequent separation of water and $CO_2$ may take place to remove the water from the obtained fluid $CO_2$ effluent.

Preferably, the $CH_4$-comprising gaseous feed is provided at a temperature in the range of from −20 to 350° C., more preferably of from 0 to 100° C., even more preferably of from 5 to 50° C.

Preferably, the $CH_4$-comprising gaseous feed is provided at elevated pressure, preferably at least a pressure at which it is contacted with the cold body having a temperature below the sublimation temperature of $CO_2$ in the range of from −20 to 350° C., more preferably of from 0 to 100° C. By providing the $CH_4$-comprising gaseous feed at at least pressure at which it is contacted with the cold body, the need to compress the $CH_4$-comprising gaseous feed prior to contacting it with the cold body is omitted.

The porous body may be prepared from any material able to store a finite amount of cold. Preferably, such a body is made of a material having a high volumetric heat capacity to maximize the amount of energy (cold) that can be stored. Especially preferably are materials that have a volumetric heat capacity of at least $1*10^6$ J/m$^3$K, more preferably a volumetric heat capacity in the range of from $1*10^6$ to $5*10^6$ J/m$^3$K. Advantageously, the material is of relatively low cost and abundantly available. Examples of suitable materials include metals, in particular steel, stainless steel and aluminium, alumina and cordierite. Also naturally occurring pebbles can be used.

To optimize the heat transfer and solid $CO_2$ deposition it is preferred that the porous body has a high specific surface area. Preferably, the body has a specific surface area of at least 1000 m$^2$/m$^3$, preferably in the range of from 1000 to 100000 m$^2$/m$^3$, more preferably, 2000 to 50000 m$^2$/m$^3$.

The cold body, may have any temperature below the sublimation temperature of $CO_2$. In order to efficiently provide enough energy for sublimating the $CO_2$, it is preferred that the cold body has a temperature in the range of from −200 to −90° C., preferably in the range of from −175 to −100° C.

A suitable process line-up for the separation of $CO_2$ from a gaseous feed stream according to the present invention is described with reference to FIGS. 1 and 2.

Figure 1:
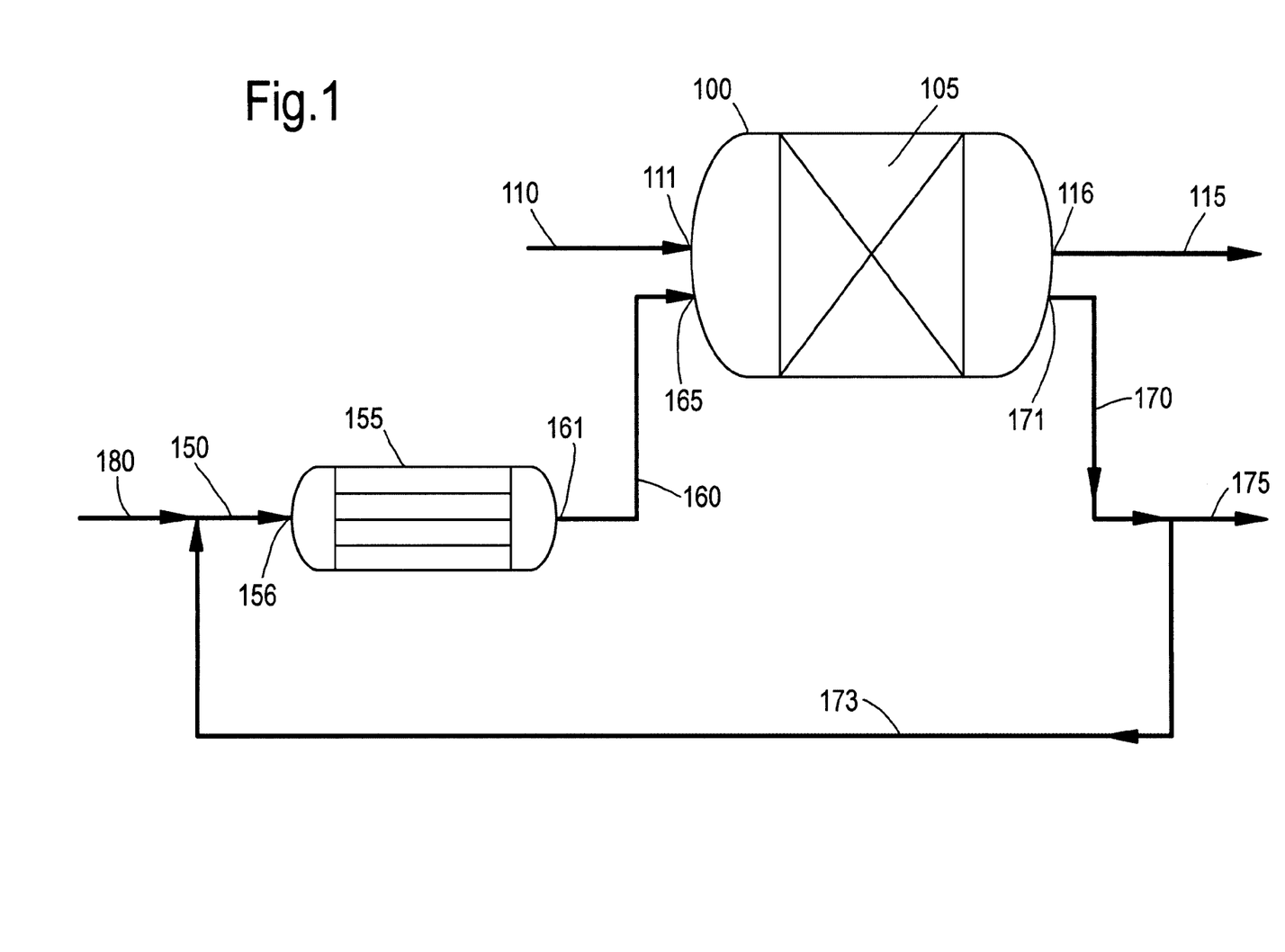
FIG. 1 provides a schematic representation of a system for the capture of $CO_2$.

In FIG. 1, a schematic representation is given of a system for the $CO_2$ capture (step (a)) and the $CO_2$ removal and cooling cycle (step (b), (c) and (d)). In FIG. 1, vessel 100 comprising fixed bed 105 of a solid packing is provided. A conduit 110 is provided for providing pressurised $CH_4$-comprising gaseous feed stream containing $CO_2$ to vessel 100 via inlet 111 during the $CO_2$-capture step. A further conduit 115 is provided to allow $CO_2$-depleted $CH_4$-comprising gaseous feed stream to exit vessel 100 via outlet 116. Optionally, one or more compressors and coolers (not shown) are provided to pressurise and cool the $CH_4$-comprising gaseous feed stream containing $CO_2$ prior to providing the feed stream to vessel 100. In addition, one or more compressors (not shown) may be provided to further pressurise the $CO_2$-depleted feed stream exiting vessel 100.

A conduit 150 is provided to supply fluid to cooler 155 via inlet 156 during the $CO_2$-removal and cooling step. A further conduit 160 is provided to remove the cold fluid from cooler 155, via outlet 161, and provide the cold fluid to inlet 165 of vessel 100, comprising fixed bed 105 of a solid packing. Conduit 170 is provided to provide heated cold fluid exiting vessel 100 via outlet 171 to be combined with the fluid in conduit 150 via conduit 173. Further conduit 175 is provided to allow any cold fluid comprising $CO_2$ to be removed from the system. Additional fluid may be provided to the system via conduit 180 to conduit 150. Optionally, a compressor (not shown) is provided in conduit 150 to increase the pressure of the fluid in conduit 150. The compressor may be located before or after the intersection of conduits 150 and 173, preferably after such intersection.

Figure 2:
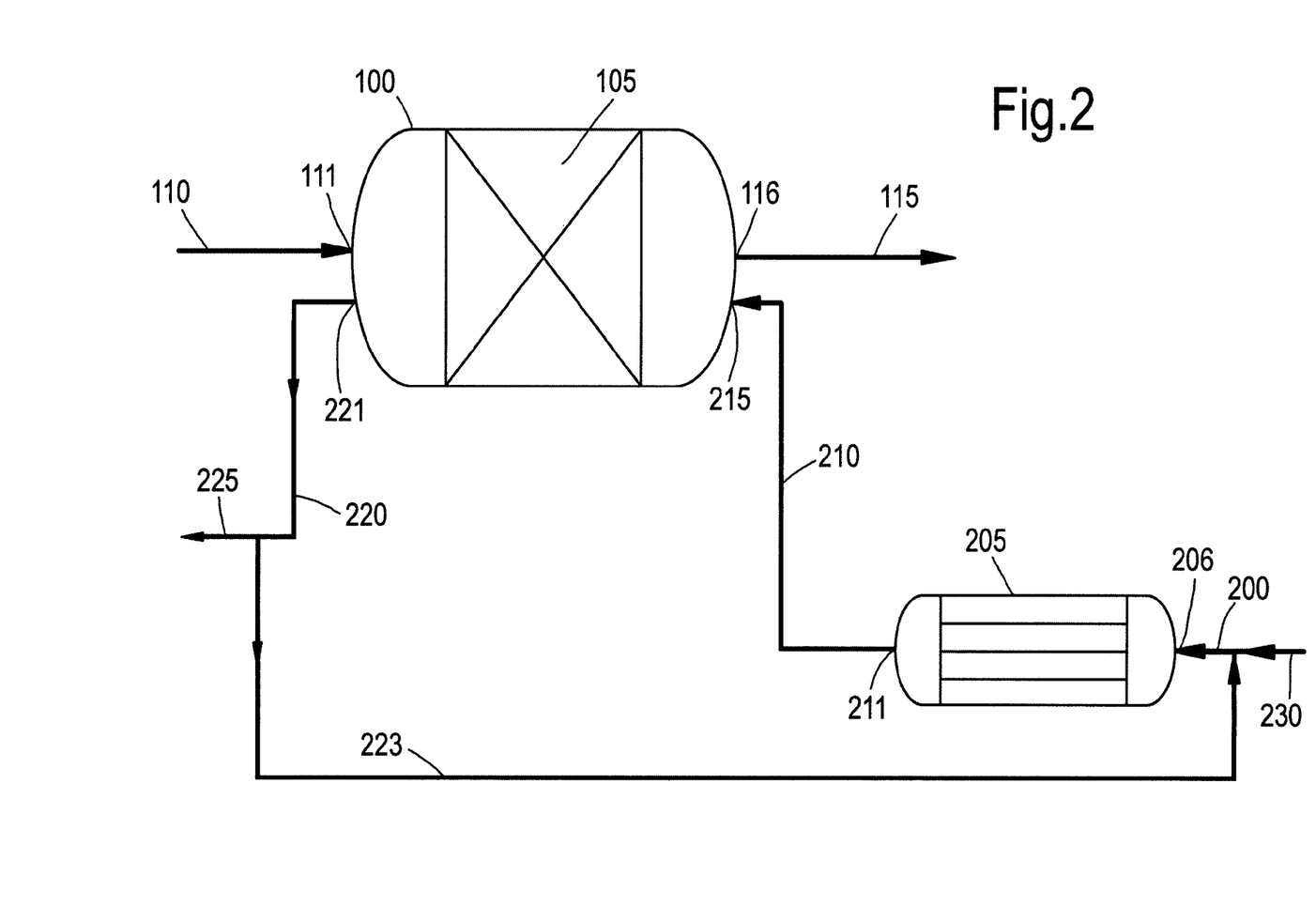
FIG. 2 provides another schematic representation of a system for the capture of $CO_2$.

In FIG. 2, a system for the $CO_2$ capture step (a) and the $CO_2$ removal and cooling cycle (step (b), (c) and (d)), suitable for passing the cold fluid in a direction opposite to the $CH_4$-comprising gaseous feed stream.

In FIG. 2, vessel 100 comprising fixed bed 105 of a solid packing is provided. A conduit 110 is provided for providing pressurised $CH_4$-comprising gaseous feed stream containing $CO_2$ to vessel 100 via inlet 111 during the $CO_2$-capture step. A further conduit 115 is provided to allow $CO_2$-depleted $CH_4$-comprising gaseous feed stream to exit vessel 100 via outlet 116. Optionally, one or more compressors and coolers (not shown) are provided to pressurise and cool the $CH_4$-comprising gaseous feed stream containing $CO_2$ prior to providing the feed stream to vessel 100. In addition, one or more compressors (not shown) may be provided to further pressurise the $CO_2$-depleted feed stream exiting vessel 100.

A conduit 200 is provided to supply fluid to cooler 205 via inlet 206 during the $CO_2$-removal and cooling step. A further conduit 210 is provided to remove the cold fluid from cooler 205, via outlet 211, and provide the cold fluid to inlet 215 of vessel 100, comprising fixed bed 105 of a solid packing. Conduit 220 is provided to provide heated cold fluid exiting vessel 100 via outlet 221 to be combined with the fluid in conduit 200 via conduit 223. Further conduit 225 is provided to allow any cold fluid comprising $CO_2$ to be removed from the system. Additional fluid may be provided to the system via conduit 230 to conduit 200. Optionally, a compressor (not shown) is provided in conduit 200 to increase the pressure of the fluid in conduit 200. The compressor may be located before or after the intersection of conduits 200 and 223, preferably after such intersection.

It will be appreciated that FIGS. 1 and 2 give a schematically representation. In order to allow or halt the supply of either the feed stream or the (cold) fluid stream, valves (not shown) may be introduced in respective conduits to and from vessel 100 or at any other suitable location in the system.

Preferably, cylindrical stainless steel vessels with cryogenic insulation material are used to hold the fixed bed. It will be appreciated that the vessels must be designed such that they can withstand operating temperatures in the range of −150° C. to 300° C. In addition, the vessels must be designed such that they can withstand the operating pressures and the pressure drop effectuated in step (b) of the process according to the invention. This may for instance require the use of specific welding techniques and limits the choice in construction materials.

The inlet and outlet for fluid arranged to receive or transfer fluids having a temperature below the sublimation temperature of $CO_2$ should preferably be able to withstand temperatures in the range of from −150° C. to ambient whereas the inlet and outlet for fluids arranged to receive or transfer fluids having a temperature above the sublimation temperature of $CO_2$ should withstand temperatures in the range of from −80 to 300° C. Preferably the inlets and outlets are insulated to prevent energy losses.

Preferably, the system as shown in FIGS. 1 and 2 comprises two vessels arranged to pass through a cycle of steps:
i) steps (a); and
ii) (b), (c) and optionally (d),
simultaneously and out of phase in each vessel.
Alternatively, the vessel comprises two fixed beds each operated, simultaneously but out of phase, according to the above mentioned cycle of the process according to the invention. It will be appreciated that the two fixed beds may also be two parts, sections or zones of a larger fixed bed arrangement inside the vessel.

EXAMPLES

The invention is illustrated by the following non-limiting examples.

Example 1

Figure 3:
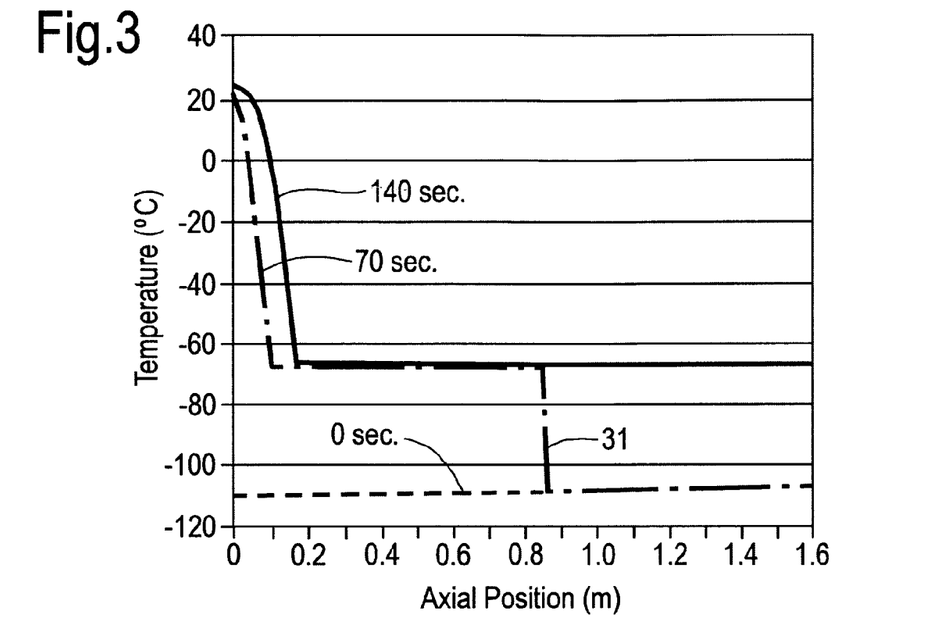
FIG. 3 provides a graphical representation of a temperature profile in a packed bed during $CO_2$ deposition.
Figure 4:
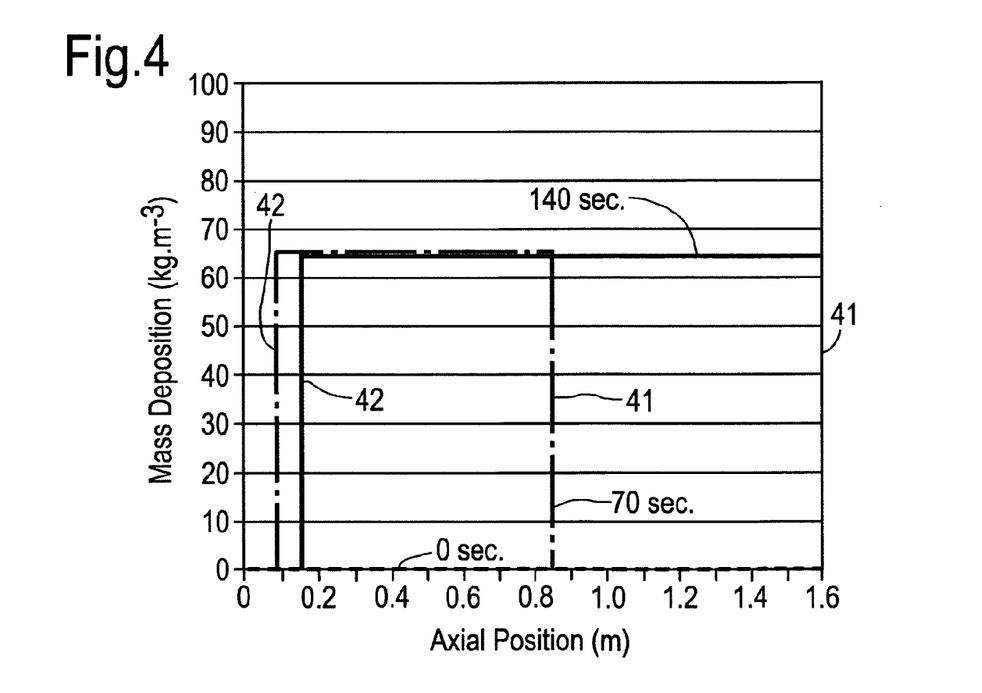
FIG. 4 provides a graphical representation of a mass deposition profile in a packed bed during $CO_2$ deposition.

The basic principle of the process for cryogenic $CO_2$ separation via dynamically operated fixed beds is depicted in FIGS. 3 and 4. The separation process is illustrated using a numerical model, wherein an effective separation between $CO_2$ and the permanent gases is achieved on the basis of differences in sublimation temperature. FIGS. 3 and 4 are based on the outcome of the model for a packed bed comprising a stainless steel monolith having a porosity of 70%. The initial temperature of fixed bed was −110° C. The fixed bed has a length of 1.65 m and a radius of 0.3 m. The feed stream was provided at a temperature of 25° C. and a pressure of 5 bar. The feed stream comprised 55 vol % $CH_4$ and 45 vol % $CO_2$, based on the volume of the feed stream. The flow rate of the feed stream was 16 000 SLPM (standard liters/minute) (0.312 kg/s). The obtained product purity was 99.1 vol %. Based on the model the temperature and mass deposition profile were modelled. In FIG. 3, the temperature profile in the fixed bed is shown at several time intervals. In FIG. 4, the mass deposition profile in the fixed bed is shown at the same time intervals.

As the warm feed stream enters the fixed bed, solid $CO_2$ and a first equilibrium temperature front 31 and first mass deposition front 41 develop in the fixed bed. At the most downstream end of the temperature and mass deposition fronts, i.e. there where the temperature transition from −110° C. to −69° C. occurs, $CO_2$ is constantly being deposited. As more feed stream, and thus more $CO_2$, enters the fixed bed the mass deposition front 41 moves toward the end of the fixed bed. At the same time, a second mass front 42 is formed as the fixed bed at the entrance is heated by the warm feed stream to a temperature above the sublimation temperature of $CO_2$. At the second more upstream mass front 42 the deposited $CO_2$ sublimates and is again deposited at the forward mass front downstream. The front velocity of first mass deposition front 41 is larger than that of second mass, corresponding to the growing amount of $CO_2$ deposited onto the fixed bed during the capture cycle. At 0 seconds the whole fixed bed is at −110° C. and no $CO_2$ is yet deposited. After 70 seconds of providing feed to the fixed bed, a first downstream mass deposition front 41 has formed at an axial position of 0.85 m. After 140 seconds the first mass deposition front 41 has reached the end of the fixed bed and breakthrough of $CO_2$ is imminent. At the moment, the forward mass deposition front 41 reaches the end of the fixed bed, supply of feed stream is halted and the bed operation is switched to remove the deposited $CO_2$ from the fixed bed.

It is noted that the amount of $CO_2$ sublimated per unit volume solid packing of the fixed bed reaches a maximum, which corresponds to the maximum amount of cold stored in the solid packing (i.e. the difference between the dew temperatures and the initial temperature). For $CO_2$ sublimation with an initial temperature of −110° C., the maximum $CO_2$ mass deposition is typically below 75 kg/m$^3$, depending on the volumetric heat capacity of the solid packing. As mentioned herein before, such amounts of solid $CO_2$ can easily be stored in a structured or unstructured packing. Thus, problems with plugging or unacceptable pressure drop increase during the capture cycle can be intrinsically circumvented.

Another important benefit of the porous body/fixed bed embodiment of the process according to the invention is that the outlet gas temperature is at the very minimum temperature of the refrigerant during almost the entire capture cycle, so that during almost the entire cycle the maximum possible $CO_2$ capture is actually achieved.

Figure 5:
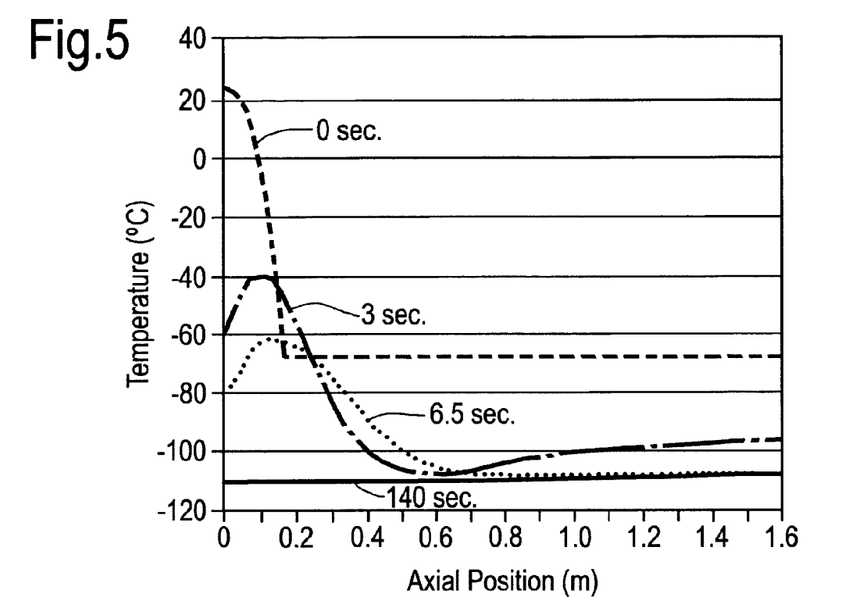
FIG. 5 provides a graphical representation of a temperature profile in a packed bed during $CO_2$ removal from the packed bed.
Figure 6:
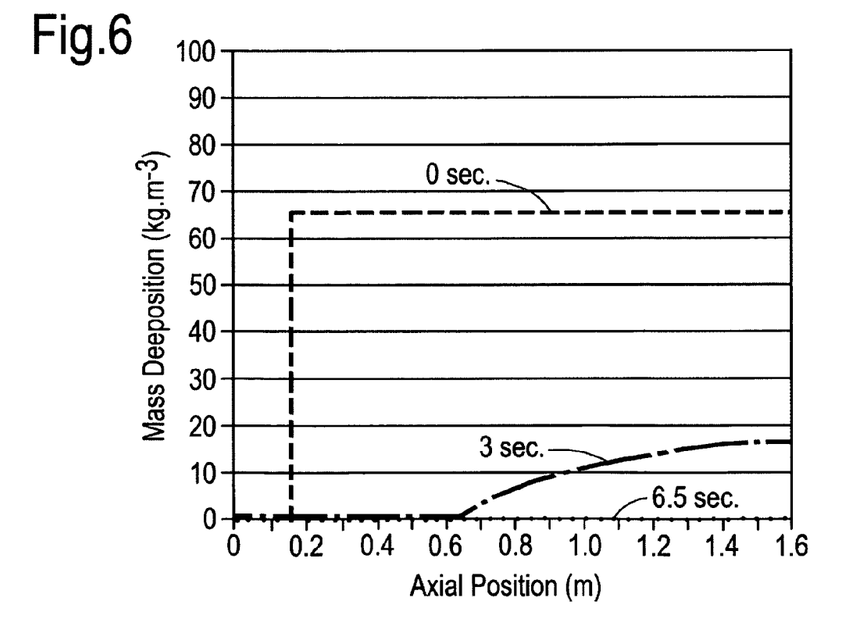
FIG. 6 provides a graphical representation of a mass deposition profile in a packed bed during $CO_2$ removal from the packed bed.

In FIGS. 5 and 6, the temperature and mass deposition profiles in the fixed bed are shown at several time intervals during the $CO_2$ removal and cooling cycle. Based on the same model the pressure was released to 1 bar at the start of the cycle (0 seconds) and dry air was fed to the fixed bed at a temperature of −110° C. and a feed rate of 5 kg/s.

It can be seen from FIG. 6 that after as little as 6.5 seconds all deposited solid $CO_2$ has sublimated. And will be removed from the fixed bed with the dry air stream.

After approximately 140 seconds the whole of fixed bed is cooled to −110° C., and can be reused to capture $CO_2$.

Example 2

With reference to FIGS. 1 and 2, the difference in energy consumption has been calculated for:
2a) a model process wherein during the $CO_2$ removal and cooling cycle (step (b), (c) and (d)), the cold fluid is passed into and through the fixed bed in the same direction as the feed stream during the capture cycle (step (a)))), i.e. co-current mode;
2b) a model process wherein during the $CO_2$ removal and cooling cycle (step (b), (c) and (d)), the cold fluid is passed into and through the fixed bed in the opposite direction compared to the feed stream during the capture cycle (step (a)), i.e. counter-current mode.

The calculations were done using the numerical method described in Tuinier et al., Chemical Engineering Science 65 (2010) 114-119 (DOI: 0.1016/j.ces. 2009.01.055). In both processes 2a and 2b, a feed stream comprising 55 vol % of $CH_4$ and 45 vol % $CO_2$, based on the volume of the feed stream is provided at a temperature of 25° C. and 2 bar absolute. The flow rate of the feed stream was 16.000 SLPM (standard liters/minute) (0.312 kg/s). The feed stream is compressed to 5 bar absolute and subsequently cooled back to 25° C. This stream is provided to a fixed bed comprising a stainless steel packing having a temperature of −110° C. The product stream exiting the fixed bed has a purity of 99.1 vol % $CH_4$ and a pressure of 4.9 bar absolute. The average temperature of the product stream is −105° C. The product gas is subsequently pressurised to obtain a product gas having a pressure of 200 bar absolute and a temperature of 215° C.

In model process 2a, after the full capacity of the fixed bed for $CO_2$ deposition is reached, a stream of cold dry air, comprising no water, having a temperature of −110° C. and a pressure of 1.05 bar absolute is provided to the fixed bed at a flow rate of 5 kg/s and in the same flow direction as the feed stream during the capture cycle. During the initial stages of the process, a heated air stream comprising $CO_2$ exits the fixed bed at an average temperature of −96° C. and a pressure of 1 bar absolute. This stream is flushed from the system. When all $CO_2$ is removed from the fixed bed, a heated air stream comprising no $CO_2$ exits the fixed bed at a temperature of −102° C. and a pressure of 1 bar absolute. This air stream is recycled to the fixed bed. Prior to entering the fixed bed, fresh dry air, comprising no water, and having a temperature of 25° C. and a pressure of 1 bar absolute is added to the recycled heated air stream to replace the air flushed from the system together with the $CO_2$. For ease of calculation, the supply of fresh air necessary to replace the air flushed from the system with the $CO_2$ is modelled as a continuous fresh air supply of which the total volume is equal to the air volume flushed from the system together with the $CO_2$. By modelling a continuous fresh air supply instead of a staged air supply, the additional power duty of the air compressor and cooler, described herein below, in the initial stage of the process is averaged over the whole process. The combined air stream of fresh air and recycled heated air has a temperature of −96° C. and a pressure of 1 bar absolute. This air stream is compressed in a compressor to 1.1 bar absolute resulting in a rise of the temperature of the air stream to −89° C. The pressurised air stream is cooled in a cooler to provide the stream of air steam and a cooled to provide the stream of cold dry air, comprising no water, having a temperature of −110° C. and a pressure of 1.05 bar absolute that is provided to the fixed bed in order to cool the fixed bed to a temperature of −110° C. This process is continued until the temperature of the fixed bed is again −110° C. In Table 1 the calculated total power consumption for removing the deposited $CO_2$ and cooling the fixed bed to −110° C. is shown.

In model process 2b, after the full capacity of the fixed bed for $CO_2$ deposition is reached, a stream of cold dry air, comprising no water, having a temperature of −110° C. and a pressure of 1.05 bar absolute is provided to the fixed bed at a flow rate of 3 kg/s and in flow direction counter-currently, i.e. opposite, to the flow direction of the feed stream during the capture cycle. During the initial stages of the process a heated air stream comprising $CO_2$ exits the fixed bed at an average temperature of −24° C. and a pressure of 1 bar absolute. This stream is flushed from the system. When all $CO_2$ is removed from the fixed bed, a heated air stream comprising no $CO_2$ exits the fixed bed at a temperature of −107° C. and a pressure of 1 bar absolute. This air stream is recycled to the fixed bed. Prior to entering the fixed bed, fresh dry air, comprising no water, and having a temperature of 25° C. and a pressure of 1 bar absolute is added to the recycled heated air stream to replace the air flushed from the system together with the $CO_2$. For ease of calculation, the supply of fresh air necessary to replace the air flushed from the system with the $CO_2$ is modelled as a continuous fresh air supply of which the total volume is equal to the air volume flushed from the system together with the $CO_2$. By modelling a continuous fresh air supply instead of a staged air supply the additional power duty of the air compressor and cooler, described herein below, in the initial stage of the process is averaged over the whole process. The combined air stream of fresh air and recycled heated air has a temperature of −97.2° C. and a pressure of 1 bar absolute. This air stream is compressed in a compressor to 1.1 bar absolute resulting in a rise of the temperature of the air stream to −90.5° C. The pressurised air stream is cooled in a cooler to provide the stream of air steam and a cooled to provide the stream of cold dry air, comprising no water, having a temperature of −110° C. and a pressure of 1.05 bar absolute that is provided to the fixed bed in order to cool the fixed bed to a temperature of −110° C. This process is continued until the temperature of the fixed bed is again −110° C. In Table 1 the calculated total power consumption for removing the deposited $CO_2$ and cooling the fixed bed to −110° C. is shown.

TABLE 1

| Step | Model process 2a | Model process 2a |
|---|---|---|
| Flow direction | Co-current to feed stream | Counter-current to feed stream |
| Required air flow [kg/s] | 5 | 3 |

| | Power consumption | |
|---|---|---|
| | kW | kW |
| Feed stream compression of 5 bar | 37.9 | 37.9 |
| Product stream compression to 200 bar | 62.6 | 62.6 |
| Air recycling | 34.2 | 20.4 |
| Cooling power | 256 | 142.5 |
| Total power consumption | 390.7 | 263.4 |

The total energy requirement for the process according to example 2a, i.e. operated with the $CO_2$ recovery and cooling cycle in co-current mode, is much higher than the total energy requirement for the process according to example 2b, i.e. operated with the $CO_2$ recovery and cooling cycle in counter-current mode, as can be seen from table 1. The calculated energy consumption for the process of example 2a is 4.3 MJ/kg $CH_4$, while the calculated energy consumption for the process of example 2b is 2.9 MJ/kg $CH_4$. The difference in the energy requirements are mainly caused by the cooling step. A relatively large air flow of 5 kg/s is required in example 2a to cool down the fixed bed to −110° C. When taking a closer look at the temperature profiles in FIG. 3, it can be observed that a hot zone is created during the capture cycle (step (a)) at the inlet of the bed, where the fixed bed is at the feed stream inlet temperature of 25° C. During the $CO_2$ removal and cooling cycle, this hot zone is moved through the entire fixed bed, when proving the cold air in the same flow direction as the feed stream, i.e. in co-current mode. Therefore, it is more efficient to reverse the flow direction during the $CO_2$ recovery and cooling cycle as illustrated in example 2b, i.e. operate the $CO_2$ recovery and cooling cycle in counter-current mode. Due to the fact that the hot temperature zone exits the fixed bed, without passing through the entire length of the fixed bed, the bulk of the fixed bed remains cold and a significantly lower cold air flow is required to cool the fixed bed. In addition, the initial stream comprising air and the removed $CO_2$ purged from the system is obtained at a significantly higher temperature, compared to example 2a, thereby reducing the loss of cold. In example 2b, a cold air flow of 3 kg/s was sufficient to cool the fixed bed back to $-110°$ C.

The lower flow rate of the air causes lower power consumption for compressor (included in under air recycling in Table 1). While both the lower flow rate of the air and the lower temperature of the air exiting the fixed bed following the initial air and $CO_2$ purge stage, causes lower power consumption of the cooler.

Example 3

Hydrogen Sulphide Removal

Simulations showing the possibility of simultaneously removing $H_2S$ using the process of the present invention.

Figure 7A:
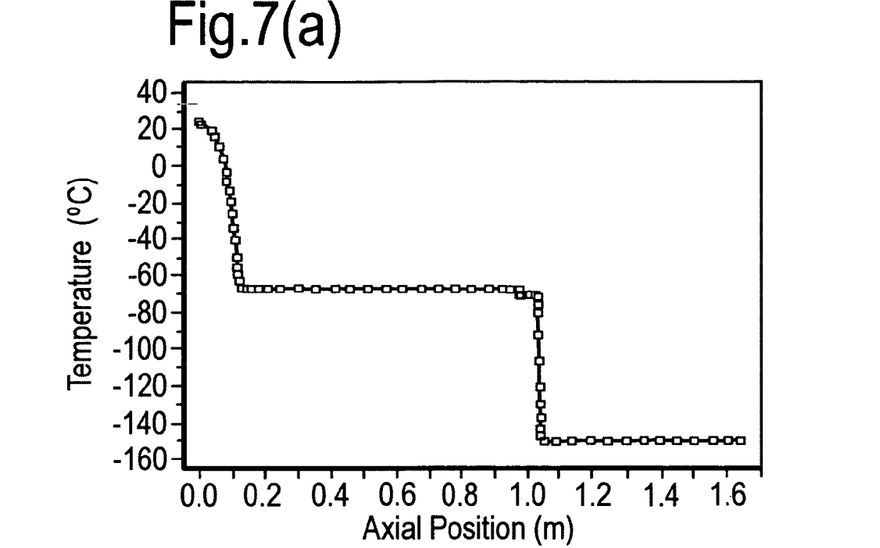
FIG. 7 provides a graphical representation of simulated (a) axial temperature and (b) mass deposition profiles after 140 seconds when feeding a $CH_4/H_2S/CO_2$ mixture to an initially refrigerated bed.
Figure 7B:
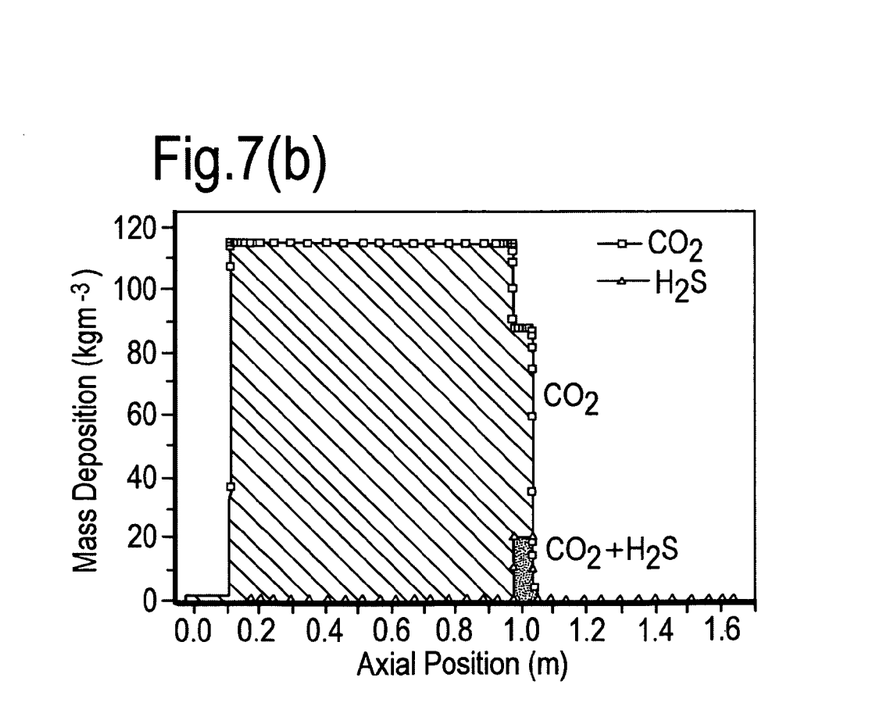

The $H_2S$ content in biogas typically ranges from 0-3 vol. %. When feeding a mixture containing 1 vol. % of $H_2S$, 45 vol. % of $CO_2$ and 54 vol. % of $CH_4$ to a cryogenically refrigerated bed (equal conditions and properties as those mentioned in Example 1), $CO_2$ and $H_2S$ can be separated simultaneously. However, with a bed temperature of $-110°$ C. the $H_2S$ content can only be reduced to 0.6 vol. %. If deep $H_2S$ removal is required, the initial bed temperature should be lower. The $H_2S$ content can be reduced to 40 ppmw when the initial bed temperature is $-150°$ C. FIG. 7 shows the resulting axial temperature and mass deposition profiles when feeding the mixture to a bed initially cooled to $-150°$ C.

Figure 8:
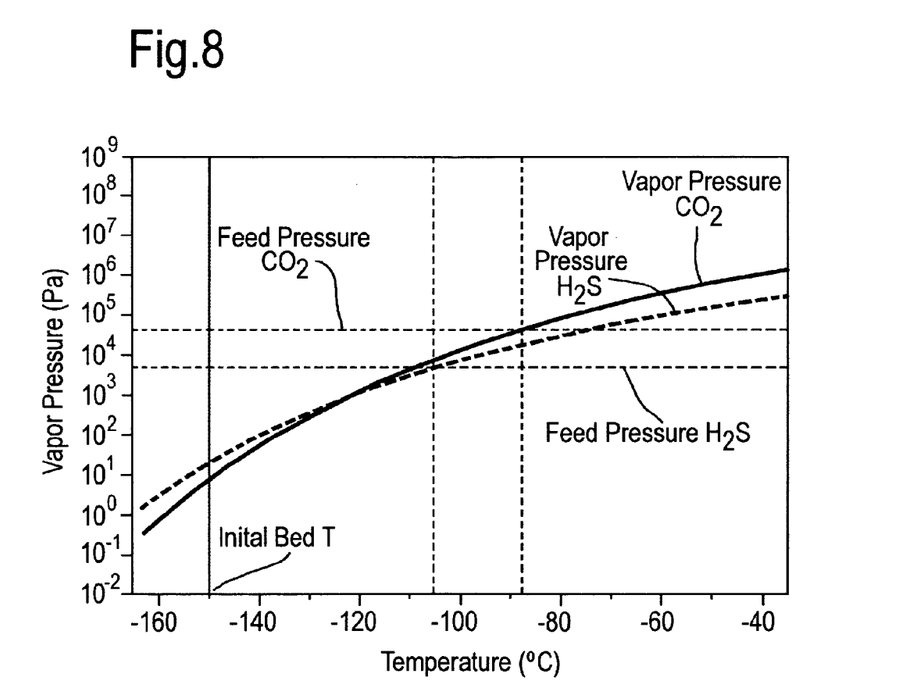
FIG. 8 provides a graphical representation of the saturation vapour pressures of $CO_2$ and $H_2S$ as a function of the temperature.

It can be observed, that both $CO_2$ as well as $H_2S$ will deposit onto the packing surface, although the zone where $H_2S$ deposits also contains $CO_2$. This can be explained by having a closer look at the saturation vapour pressures of both components in FIG. 8. When the mixture is cooled down, $CO_2$ starts to deposit at $-88°$ C., as indicated by the dotted line. The temperature will decrease further and below $-105.1°$ C. the saturation vapour pressure of $H_2S$ becomes lower than its partial pressure in the feed (0.05 bar) and $H_2S$ starts to deposit as well. During the cooling of the mixture from $-105.1°$ C. to the initial bed temperature, both components will deposit onto the packing. Therefore, it can be concluded that components with saturation vapour pressure close together will deposit in the same region. Nevertheless, these results show that both components can be efficiently removed from the feed gas.

What is claimed is:

1. A process for the separation of a contaminant or mixture of contaminants from a $CH_4$-comprising gaseous feed stream, comprising the subsequent steps of:
   a) passing a $CH_4$-comprising gaseous feed stream comprising the contaminant or the mixture of contaminants into and through a cold porous body having a temperature below the sublimation temperature of the contaminant or the mixture of contaminants and contacting the $CH_4$-comprising gaseous feed stream at elevated pressure with the surface of the cold porous body to obtain a porous body comprising solid contaminant or mixture of contaminants and a contaminant-depleted product gas; and
   b) reducing the pressure to obtain fluid contaminant or mixture of contaminants and the cold porous body,
   c) removing the fluid contaminant or mixture of contaminants,
   wherein the contaminant is selected from $CO_2$, hydrogen sulphide, mercaptans, siloxanes and carbonyl sulphide, or a mixture thereof.

2. A process according to claim 1 wherein the contaminant comprises $CO_2$ and wherein steps a) through c) comprise, respectively:
   a) passing the $CH_4$-comprising gaseous feed stream comprising $CO_2$ into and through the cold porous body having a temperature below the sublimation temperature of $CO_2$ and contacting the $CH_4$-comprising gaseous feed stream at a pressure of at least 4 bar absolute with the surface of the cold porous body to obtain a porous body comprising solid $CO_2$ and a $CO_2$-depleted product gas;
   b) reducing the pressure by at least 2 bar to obtain fluid $CO_2$ and the cold porous body; and
   c) removing the fluid $CO_2$.

3. A process according to claim 2, further including a step:
   d) passing a cold fluid stream having a temperature below the sublimation temperature of $CO_2$, into and through the cold porous body to further cool the cold porous body.

4. A process according to claim 2, wherein step (c) and (d) are combined to simultaneously remove the fluid carbon dioxide and further cool the cold porous body.

5. A process according to claim 3, wherein the $CH_4$-comprising gaseous feed stream comprising $CO_2$ is passed into and through the cold porous body in step (a) in a first flow direction and cold fluid stream is passed into and through the cold porous body in step (c) and/or (d) in a flow direction opposite to the flow direction of the $CH_4$-comprising gaseous feed stream.

6. A process according to claim 3 wherein the cold fluid stream gaseous stream is cold nitrogen or dry air.

7. A process according to claim 2, wherein the $CH_4$-comprising gaseous feed stream is contacted with the surface of the cold body at a pressure in the range of from 4 to 50 bar absolute.

8. A process according to claim 2 wherein in step (b) the pressure is reduced by in the range of from 2 to 49 bar.

9. A process according to claim 1 comprising providing two porous bodies in the form of two fixed beds and passing the beds through a cycle of steps:
   (a); and
   (b), and (c),
simultaneously and out of phase.

10. A process according to claim 1 wherein the temperature of the cold body having a surface is in the range of from $-200$ to $-90°$ C.

11. A process according to claim 1 wherein the $CH_4$-comprising gaseous feed stream further comprises $H_2O$ and/or $H_2S$.

12. A process according to claim 1 wherein the body having a surface has a specific surface area of at least 1000 $m^2/m^3$.

13. A process according to claim 1 wherein the body having a surface comprises a ceramic or metal.

* * * * *